United States Patent [19]

Brussee et al.

[11] Patent Number: 5,412,119

[45] Date of Patent: May 2, 1995

[54] METHOD OF PREPARING VICINAL AMINOALCOHOLS

[75] Inventors: Johannes Brussee; Arne van der Gen; Chris G. Kruse, all of Weesp, Netherlands

[73] Assignee: Duphar International Research B.V., Weesp, Netherlands

[21] Appl. No.: 11,547

[22] Filed: Feb. 1, 1993

[30] Foreign Application Priority Data

Feb. 4, 1992 [EP] European Pat. Off. ............ 92200310

[51] Int. Cl.$^6$ .................. C07D 315/00; C07C 215/00
[52] U.S. Cl. .................................. 549/419; 549/475; 564/355; 564/356
[58] Field of Search ................ 564/355, 356; 549/419, 549/475

[56] References Cited

U.S. PATENT DOCUMENTS 4,119,710 10/1978 Engelhardt et al. ................. 424/282
4,629,737 12/1986 Cantello .............................. 514/564

FOREIGN PATENT DOCUMENTS 0104888 4/1984 European Pat. Off. .
0142070 5/1985 European Pat. Off. .
853166 10/1952 Germany .

OTHER PUBLICATIONS

Chemical Abstracts, vol. 107, US, Abstract No. 194876, Huneck, S., et al, "Aromatic Compounds from Oxytropis Pseudoglandulosa" (1987).
Chemical Abstracts, vol. 90, US, Abstract No. 222, Fristrom, Sinikka, et al., "Release of Platelet 5-Hydroxytryptamine by Some Anorexic and other Sympathomimetics and their acetyl derivatives" (1979).
Pharmazie, 46(6), 426–31, 1991, Raether, Gisela, et al., "Effects of Antioxidants on the Degradation Mechanism of Epinephrine Solutions".
J. Pharm. Pharmacol., 22(7), 512–17, 1970, Forrest, Janet E., et al, "Nuclear Magnetic Resonance Spectroscopy of the Trimethylsilyl ethers of some Hydroxyphenylalkylamines".
Tetrahedron Letters, vol. 31, No. 5, 1990, GB, pp. 601–604, Corey, E. J., et al, "The First Enantioselective Synthesis of Pure R– and S–Isoproterenol".
Tetrahedron, 48(19), 3977–82, 1992, Zandbergen, Peter, et al., "A One-Pot Reduction-Transimination-Reduction Synthesis of N–Substituted β-Ethanolamines from Cyanohydrins".
Patent Abstracts of Japan, vol. 4, No. 61 (C–009) 8 May 1980 & JP–A–55 028 914 (Tanabe Seiyaku Co. Ltd.).
Helvetica Chimica Acta, vol. 71, 1988, Basel CH, pp. 320–336, Goodman et al, "Optically Pure Isoproterenol Analogues . . . ".
Tetrahedron Letters, vol. 31, No. 5, 1990, Exford GB, pp. 601–604; Corey et al, "The First Enantioselective . . . ".
Journal of Organic Chemistry, vol. 56, 1991, Washington DC, US, pp. 442–444, Corey et al, "A Catalytic Enantioselective . . . ".
Helvetica Chimica acta, vol. 61, No. 8, 1978, Basel CH, pp. 3028–3037, Fischli, "287, COB(I)Alamin Als Katalysator . . . ".
Recueil des Travaux Chimiques des Pays–Bas, vol. 110, No. 1, Jan. 1991, Den Haag NL, pp. 25–26, Brussee et al.

Primary Examiner—C. Warren Ivy
Assistant Examiner—A. A. Owens
Attorney, Agent, or Firm—Stevens, Davis, Miller & Mosher

[57] ABSTRACT

The present invention is concerned with the preparation of N-substituted vicinal aminoalcohol derivatives from the corresponding hydroxyl-protected cyanohydrin derivatives by successive partial reduction, transimination using a primary amine, reduction of the resulting imine and optional removal of the hydroxyl-protecting group. The products are obtained either as a racemate or in an optically pure form, depending upon the stereochemical composition of the starting cyanohydrin derivatives.

The present invention is also concerned with certain new enantiomerically pure hydroxyl-protected vicinal aminoalcohols.

6 Claims, No Drawings

METHOD OF PREPARING VICINAL AMINOALCOHOLS

The invention relates to a method for the preparation of vicinal aminoalcohols and to optically active O-protected derivatives thereof.

A large number of pharmaceutically active agents belong to the class of phenyl or phenoxy substituted vicinal amino-alcohol derivatives, e.g. the $\beta$-adrenergic agents propranolol, timolol, nifenalol, sotalol, isoproterenol and denopamine.

All these active agents contain a chiral centre in their molecular structure and therefore give rise to optical isomerism. It is generally known in the art that only one of the enantiomers displays the desired biological activity (the so-called eutomer) and that the presence of the optical antipode may lead to side effects. Therefore, it is generally deemed more and more desirable to administer the biologically active agent in the form of its pure eutomer rather than the racemic mixture.

The classical method for the preparation of racemic vicinal aminoalcohols consists of a reduction of the corresponding aminoketones. The alternative method of the reductive amination of the corresponding hydroxyaldehydes has not been practiced in view of the known instability of the latter class of compounds.

For the preparation of enantiomerically pure vicinal aminoalcohols a number of alternative methods are possible. Optical resolution by chemical or enzymatic methods however leaves the problem behind of the unwanted isomer, that should be recycled into the process.

Obviously, the use of a chiral precursor is the preferred method. This is illustrated by Corey and Lerik (*J. Org. Chem.* 1991, 65, p.442) who prepared an optically pure O-silylated aminoalcohol by a lengthy procedure with the aid of a chiral catalyst. Furthermore, they show the possibility to use this protected aminoalcohol as a precursor for the enantiomerically pure biologically active agent by a deprotection step. The synthesis of O-silylated aminoalcohols and their subsequent deprotection are described in EP-A-0104888, using chiral epoxides, generally difficult of access, as starting compounds.

The present invention relates to a simple one-step procedure of preparing both protected and unprotected aminoalcohols, either as a racemate or in an enantiomerically pure form starting from readily available racemic or chiral pure cyanohydrins.

According to the present invention an N-substituted vicinal amino-alcohol derivative of formula 1

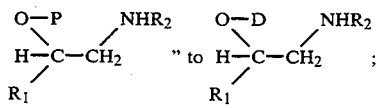

wherein

D is a group protecting the hydroxyl group;
$R_1$ is a monocyclic or bicyclic aryl or heteroaryl group substituted with one or more groups X, wherein X is hydroxy, alkoxy(1-5C), alkyl(1-5C)carbonyloxy, amino, alkyl(1-5C)carbonylamino, alkyl(1-5C)sulphonylamino, nitro, alkyl(1-5C)sulphonyl, alkyl(1-5C)carbonyl, halogen, cyano, alkyl(1-5C) or cycloalkyl(5-12C), or wherein $R_1$ is a saturated or unsaturated straight or branched alkyl group having 1-30 C-aroms which may be substituted with halogen, alkoxy(1-5C), alkylthio(1-5C), phenyl or phenoxy optionally substituted with one or more groups X, and
$R_2$ is a hydrogen arom or a saturated or unsaturated straight or branched alkyl(1-10C) group, optionally substituted with halogen, hydroxy, alkoxy(1-4C) or OP, or a phenyl, phenylalkyl(7-10C) or heteroarylalkyl(1-3C for the alkyl) group, optionally substituted with one to three groups X,
or wherein $R_2$ has the general formula 7

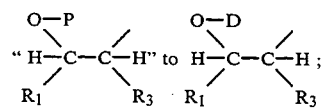

wherein $R_3$ is hydrogen or alkyl(1-4C); is prepared by reacting a hydroxyl-protected cyanohydrin derivative of formula 2

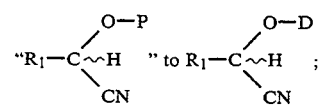

with a reducing reagent of formula 3

wherein

A represents a hydrogen arom or a metal arom selected from the group of alkali, earth alkali or early transition metal aroms,
R is an alkyl(1-6C), alkoxyalkyl(1-6C) or alkoxy(1-6C) group, and
m is, dependent on the valence of A, 0-2; yielding a partially reduced compound of formula (4)

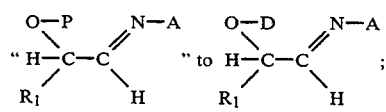

followed by a transimination reaction using a primary amine of formula 5

and reduction of the resulting imine, wherein D, $R_1$ and $R_2$ have the abovementioned meanings;
with the proviso that, if $R_2$ is a hydrogen arom, the transimination reaction step is omitted.

A comparable procedure including a transimination reaction has recently been described by Brussee et al.- (Recl. Trav. Chim. Pays-Bas 1991, 25, p. 110) for the preparation of products of formula 6, having an additional substituent R in the aminoalcohol chain compared with the above formula 1 compounds.

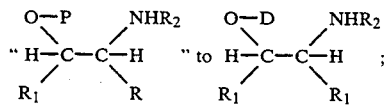

It is however not obvious that application of this method to products where R has been replaced by a hydrogen arom would lead to acceptable results. For this analogous procedure a partial reduction of the protected cyanohydrin to produce the intermediate compound of general formula 4 should be carried out as the first step. However, Panunzio et al. (Tetrahedron Letters 1990, 31, p. 3841) and Schlosser et al.(Helv. Chim. Act. 1978, 61, p. 1903) describe moderate to very poor results for this transformation starting from racemic protected cyanohydrins, since the protected hydroxyaldehydes—resulting from immediate and quantitative hydrolysis of the compound of formula 4—or products of the general formula 6, resulting from an addition reaction with an R-metal reagent, were only isolated in low yields.

Moreover, application of this method to enantiomerically pure protected cyanohydrins was reported to lead to partial racemization by Effenberger et al. (Chem. Ber. 1991, 124, p. 1651).

It is therefore surprising that the method according to the present invention not only gives high to excellent over-all yields of the vicinal aminoalcohols but also shows no loss of optical purity. Consequently, after the last reduction step the protected aminoalcohols of formula (1) can be isolated in high yields (usually >80%) in a one-pot procedure, so after the above reaction sequence without isolation of the intermediates. The method according to the present invention avoids the lengthy procedures described in the art and makes use of the smooth reductive amination procedure on the imine intermediate (4) without the necessity of isolating the corresponding unstable $\beta$-hydroxyaldehydes.

Moreover, by carrying out partial reduction under carefully controlled reaction conditions racemization of the starting enantiomerically pure cyanohydrins can be completely suppressed.

This partial reduction can be carried out with organometallic reagents containing an active hydrogen arom or with hydrogen and a selected metallic catalyst.

Suitable organometallic reagents are e.g. aluminium or boron hydrides, such as diisobutylaluminium hydride (DIBAL) or sodium di(2-methoxyethoxy) aluminium hydride. These reductions are preferably carried out in apolar solvents such as ethers, tert. amines, alkanes or aromatics or mixtures thereof.

The transimination reaction of intermediate (4) is preferably carried out after the addition of a proton donating agent such as an alcohol (e.g. methanol) or an ammonium salt (e.g. ammonium bromide). This converts the imine of formula 4 into the corresponding primary imine with A replaced by hydrogen. The subsequent addition of the primary amine of formula 5 gives rise to a fast and irreversible transimination reaction under the liberation of $NH_3$, giving a secondary imine, analogous to the method described by Brussee et al. for the corresponding substituted derivatives.

The final step in this preparation involves a reduction step of the resulting imine. This reduction can be established by the usual reducing agents employed for the conversion of imines into secondary amines, e.g. as described by Harada in "The Chemistry of the Carbon-Nitrogen Double Bond". pp. 276–293. Useful examples are (earth)alkali metal aluminiumhydrides and borohydrides, (earth)alkali metals in protic solvents, and hydrogen gas in the presence of a metal catalyst. Advantageously use is made of reducing agents of the general structure $M_1M_2(Q)_nH_{4-n}$, wherein $M_1$ is a metal from the group IA or IIA of the periodic table of elements, $M_2$ is boron or aluminium, n is an integer having the value 0–3, and Q is an electron-withdrawing substituent, e.g. of the type CN, halogen, alkoxy or dialkylamino. In particular, use can be made of reagent wherein $M_2$ is boron, n is 0 or 1 and Q is CN.

Examples of suitable aryl groups for the symbol $R_1$ in the above formula 1 compounds are phenyl and naphthyl; examples of suitable heteroaryl groups for the symbols $R_1$ and $R_2$ are benzofuryl, benzodioxanyl, benzodioxolyl, and the like. Examples of suitable hydroxy-protecting groups D are: (trihydrocarbyl)silyl, (dihydrocarbyl)(hydrocarbyloxy)silyl, tert.alkyl(4–12C) , (opt. substituted)phenoxy[dialkyl(2–8C)]ethyl, alkoxy(-1–4C)[dialkyl(2–8C)]methyl, (thio)acetal-constituting groups such as di- and tetrahydropyran-2-yl and di- and tetrahydrofur-2-yl, and ester-constituting groups derived from mono-, di- or tri-substituted acetic acid, wherein the substituents are preferably selected from alkyl(1–12C) and optionally with one or more X substituted phenyl, optionally with one or more methyl substituted cyclohexanecarboxylic acid or adamantane carboxylic acid. The above term hydrocarbyl includes alkyl(1–8C), alkenyl(2–8C), alkynyl(2–8C), phenyl and phenyl substituted with one or more X. The above term (opt. substituted)phenoxy includes unsubstituted phenoxy and phenoxy substituted with one or more X.

As a further aspect of the present invention, both racemic and enantiomerically pure aminoalcohols of the general formula 8

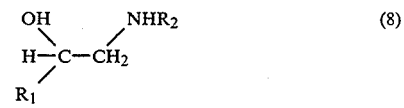

wherein the symbols have the above-defined meanings, can be obtained directly in the process according to the invention if the protecting group D is removed during the isolation procedure after the final reduction step. This can be accomplished by e.g. a treatment with aqueous acid in the case of acid-labile protecting groups, such as the above-defined silyl protecting groups, alkoxy(dialkyl)methyl groups or (subst.)phenoxy(dialkyl)methyl groups.

Preferably said deprotection is performed in such manner, that protecting group D is removed without intermediate isolation of the formula 1 compound during a work-up step following the reduction of the N-substituted imine.

Part of the resulting enantiomerically pure O-protected aminoalcohols of the general formula 1 is known, e.g. from EP-A-0104888, EP-A-0099707, JP-A-55/028914, Helvetica Chim. Acta 1988, 71, 320–336 (Goodman et al.), Tetrahedron Letters 1990, 31, 601–604 (Corey et al.) and the above-mentioned Corey et al. publication.

Part of the resulting pure enantiomers, however, is new. Therefore the present invention also relates to new enantiomerically pure aminoalcohol derivatives of the general formula 9

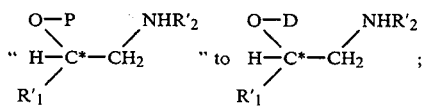

wherein
the C*-arom has either the R or the S configuration;
D has the meaning as given above;
R₁' is a phenyl group, optionally substituted with one or more substituents X as defined above; and
R₂' is a hydrogen arom or a straight or branched alkyl(1–6C) group, or wherein R₂' has the general formula 10

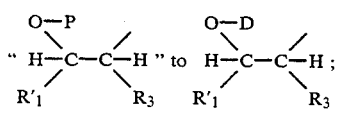

wherein R₃ is hydrogen or alkyl(1–4C).

The above new enantiomers are interesting synthons for the production of pharmacologically active preparations of the aminoalcohol structural class. Pre-eminently suitable as intermediates are compounds of the above general formula 9, wherein the protecting group D is a tert.butyl-dimethylsilyl group, a 2-phenoxy-isopropyl group, a 2-methoxy-isopropyl group, a di- or tetrahydropyran-2-yl group or a di- or tetrahydrofur-2-yl group.

The invention will now be described in greater detail with reference to the following specific examples.

EXAMPLE 1

(R)-(+)-[(2-Methoxy-isopropyl)oxy]benzeneacetonitrile 9.0 g (68 mmol) of (R)-(+)-β-hydroxybenzeneacetonitrile was dissolved in 2-methoxypropene (25 ml), one drop of POCl₃ was added and the solution was stirred for 45 minutes at room temperature. Three drops of triethylamine were added, the mixture was taken up in ether (100 ml) and washed successively with water (25 ml) and a saturated NaHCO₃ solution (25 ml). The organic phase was dried on MgSO₄ and concentrated in vacuo.

Yield: 13.75 g (99%) of a clear oil. Analytical data. ¹H-NMR (200 MHz, CDCl₃, TMS): 1.40 and 1.58 (s, 6H, C(CH₃)₂); 3.22 (s, 3H, OCH₃); 5.47 (s, 1H, CH(OR₂)); 7.43 (m, 5H, arom.). ¹³C-NMR (50 MHz, CDCl₃, CDCl₃): 24.0 and 24.6 (C(CH₃)₂); 49.5 (OCH₃); 61.1 (CH(OR₂)); 102.5 (C(CH₃)₂; 119.0 (CN); 126.7, 128.7 and 129.0 (C arom.); 134.8 (C₁ arom.). [α]$_D^{20}$=+47°(c=1 CHCl₃); e.e.>98.5% (HPLC)).

EXAMPLE 2

(R)-(+)-[(2-Methoxy-isopropyl)oxy]-4-methoxybenzeneacetonitrile

Prepared in the same manner as described in EXAMPLE 1, using (R)-(+)-(α-hydroxy-4-methoxybenzeneacetonitrile as the cyanohydrin.

Yield: 99% (colorless crystals). mp 40°–42° C. Analytical data ¹H-NMR (200 MHz, CDCl₃, TMS): 1.38 and 1.56 (s, 6H, C(CH₃)₂); 3.21 (s, 3H, OCH₃); 3.82 (s, 3H, p-OCH₃); 5.41 (s, 1H, CH(OR₂)); 6.92 (d, 2H, J=8.7 Hz, arom.); 7.40 (d, 2H, J=8.7 Hz, arom.). ¹³C-NMR (50 MHz, CDCl₃, CDCl₃): 23.9 and 24.4 (C(CH₃)₂); 49.2 (OCH₃); 54.7 (p-OCH₃); 60.5 (CH(OR₂)), 102.2 (C(CH₃)₂); 113.9 C₃ and C₅ arom.); 119.1 (CN); 126.9 (C₁ arom.); 128.1 (C₂+C₆ arom.); 158.7 (C₄ arom). [α]$_D^{20}$+41°(c=1 CHCl₃); e.e.>99% (HPLC)).

EXAMPLE 3

(R)-(−)-α-[(Methylamino)methyl]benzenemethanol, (R)-Halostachine

To a cooled (−70° C.) solution of 1.02 g (5 mmol) of the product of EXAMPLE 1 (e.e.>98.5% (HPLC)) in 40 ml of dry ether was added 12.5 ml of a 1 mol/l DIBAL solution in hexane (12.5 mmol). After stirring at −70° C. for 3 hours 1.25 g NH₄Br (12.5 mmol) in 20 ml of dry methanol was added.

The cooling bath was removed and 3 ml of an 8.03 mol/l CH₃NH₂ solution (24 mmol) in ethanol was added. Stirring was continued for 45 minutes (−70° C.→room temperature). The mixture was cooled in an ice bath and 0.37 g of NaBH₄ (10 mmol) was added in three portions. The reaction mixture was stirred overnight at room temperature. Ether (25 ml) and a 1 mol/l HCl solution (70 ml) were added and extracted. The water layer (pH=3) was basidified with 5N NaOH until a clear solution appeared and extracted with ether (4×50 ml). These four combined ether layers were dried (K₂CO₃) and concentrated to leave a clear oil.

Yield: 0.59 g (79%). Analytical data ¹H-NMR (200 MHz, CDCl₃, TMS): 2.2 (broad, 2H, OH and NH); 2.46 (s, 3H, NCH₃); 2.74 (dd, ABX, 1H, CH₂, J$_{AB}$=11.8 HZ J$_{AX}$=4.6 HZ); 2.81 (dd, ABX, 1H, CH₂, J$_{AB}$=11.8 Hz J$_{BX}$=4.6 Hz); 4.74 (dd, 1H, CH(OH), J=4.6 and 8.7 Hz); 7.32 (m, 5H, arom. ) . ¹³C-NMR (50 MHz, CDCl₃, CDCl₃): 35.6 (NCH₃); 59.0 (CH₂); 71.4 (CH(OH)); 125.6, 127.1 and 128.1 (C arom.); 143.2 (C₁ arom.).

This product was converted into the HCl salt and crystallized from iso-propanol for optical rotation and melting point measurements. [α]$_D^{20}$−53°(c=1 H₂O), literature: [α]$_D^{20}$−52.46°. mp 102°–104° C., literature mp 113°–114° C.

EXAMPLE 4

(R)-(−)-α-[(Methylamino)methyl]-α-[(tert-butyldimethylsilysilyl)oxy]benzenemethane Prepared in the same manner as in EXAMPLE 3, using R-(+)-(ter.butyldimethylsilyloxy)benzeneacetonitrile (e.e.>99% (HPLC)) as the cyanohydrin. After the NaBH₄ reduction the reaction mixture was poured into water (100 ml) and extracted with ether (3×50 ml). The combined ether layers were washed with water (50 ml), dried (K₂CO₃) and concentrated in vacuo.

Yield: 97% (clear oil). Analytical data ¹H-NMR (200 MHz, CDCl₃, TMS): −0.15 and 0.04 (s, 6H, Si(CH₃)₂); 0.89 (s, 9H, C(CH₃)₃)); 1.8 (broad, 1H, NH); 2.44 (s, 3H, NCH₃); 2.63 (dd, ABX, 1H, CH₂, J$_{AB}$=11.8 Hz, J$_{AX}$=8.2 Hz); 2.79 (dd, ABX, 1H, CH₂, J$_{AB}$=11.8 Hz, J$_{BX}$=4.1 Hz); 4.81 (dd, 1H, CH(OTBS), J=4.1 and 8.2 Hz); 7.31 (m, 5H, arom.). ¹³C-NMR (50 MHz, CDCl₃, CDCl₃): −5.0 and −4.5 (Si(CH₃)₂); 18.1 (C(CH₃)₃); 25.8 (C(CH₃)₃); 36.1 (NCH₃); 60.1 (CH₂); 74.0 (CH(OTBS)); 126.0, 127.3 and 128.1 (C arom.); 143.4 (C₁ arom.). [α]$_D^{20}$−68°(c=1 CHCl₃).

EXAMPLE 5

(R)-(−)-α-[[(1-Methylethyl)amino]methyl]benzenemethanol

Prepared in the same manner as in EXAMPLE 3, using iso-propylamine in the transimination reaction.

Yield: 74% (white solid). Analytical data ¹H-NMR (200 MHz, CDCl₃, TMS): 1.08 (d, 6H, CH(CH₃)₂), J=6.2 Hz); 1.9 (broad, 2H, OH+NH); 2.64 (dd, ABX, 1H, CH$_2$, J$_{AB}$=11.8 Hz, J$_{AX}$=8.7 Hz); 2.83 (sept., 1H, CH(CH$_3$)$_2$, J=6.2 Hz); 2.93 (dd, ABX, 1H, CH$_2$, J$_{AB}$=11.8 Hz, J$_{BX}$=3.6 Hz); 4.66 (dd, 1H, CH(OH), J=3.6 and 8.7 Hz); 7.32 (m, 5H, arom.). $^{13}$C-NMR (50 MHz, CDCl$_3$, CDCl$_3$): 23.0 (CH(CH$_3$)); 48.6 (CH(CH$_3$)$_2$); 54.8 (CH$_2$); 71.9 (CH(OH)); 125.7, 127.3 and 128.2 (C arom.); 142.4 (C$_1$ arom.).

This product was converted into the HCl salt and crystallized from iso-propanol for optical rotation and melting point measurements. [α]$_D^{20}$ −48°(c=1 H$_2$O).

EXAMPLE 6

(R)-(−)-α-[[(1-Methylethyl)amino]methyl]-α-[(tert-butyldimethylsilyl)oxy]benzenemethane Prepared in the same manner as in EXAMPLE 4, using iso-propylamine in the transimination reaction.

Yield: 96% (slightly yellow oil). Analytical data $^1$H-NMR (200 MHz, CDCl$_3$, TMS): −0.16 and 0.05 (s, 6H, Si(CH$_3$)$_2$; 0.90 (s, 9H, C(CH$_3$)$_3$)); 1.02 and 1.06 (d, 6H, CH(CH$_3$)$_2$, J=6.2 Hz); 2.3 (broad, 1H, NH); 2.72 (d, 2H, CH$_2$, J=6.2 Hz); 2.81 (sept., 1H, CH(CH$_3$)$_2$, J=6.2 Hz); 4.78 (t, 1H, CH(OTBS), J=6.2 Hz); 7.31 (m, 5H, arom.). $^{13}$C-NMR (50 MHz, CDCl$_3$, CDCl$_3$): −5.5 and −5.0 (Si(CH$_3$)$_2$); 17.6 (C(CH$_3$)$_3$); 22.2 and 22.5 (CH(CH$_3$)$_2$); 25.3 (C(CH$_3$)$_3$); 47.7 (CH(CH$_3$)$_2$); 56.0 (CH$_2$); 74.0 (CH(OTBS)); 125.5, 126.9 and 127.5 (C arom.); 143.0 (C$_1$ arom.). [α]$_D^{20}$ −63°(c=1 CHCl$_3$); e.e.>99% (HPLC)).

EXAMPLE 7

(R)-(−)-α-[(Methylamino)methyl]-4-methoxybenzenemethanol

Prepared in the same manner as in EXAMPLE 3, using the product of EXAMPLE 2 (e.e.>99% (HPLC)) as the cyanohydrin Yield: 90% of (5e) (yellow solid). Analytical data $^1$H-NMR (200 MHz, CDCl$_3$, TMS): 2.2 (broad, 2H, OH+NH); 2.47 (s, 3H, NCH$_3$); 2.70 (dd, ABX, 1H, CH$_2$, J$_{AB}$=12.3 Hz, J$_{AX}$=8.2 Hz); 2.80 (dd, ABX, 1H, CH$_2$, J$_{AB}$=12.3 Hz, J$_{BX}$=4.1 Hz); 3.81 (s, 3H, OCH$_3$); 4.69 (dd, 1H, CH(OH), J=4.1 and 8.2 Hz); 6.88 (d, 2H, arom., J=8.7 Hz); 7.29 (d, 2H, arom., J=8.7 Hz). $^{13}$C-NMR (50 MHz, CDCl$_3$, CDCl$_3$): 35.8 (NCH$_3$); 55.1 (OCH$_3$); 59.2 (CH$_2$); 71.1 (CH(OH)); 113.6 (C$_3$ and C$_5$ arom.); 126.9 (C$_2$ and C$_6$ arom.); 135.3 (C$_1$ arom.); 158.8 (C$_4$ arom.).

This product was converted into the HCl salt and crystallized from iso-propanol for optical rotation and melting point measurements. [α]$_D^{20}$ −45°(c=1 H$_2$O). mp: 137°-139° C.

EXAMPLE 8

(R)-(−)-α-[(Methylamino)methyl]-α-[(tert-butyldimethylsilyl))oxy]-4-methoxybenzenemethane Prepared in the same manner as in EXAMPLE 4, using R-(+)-(tert.butyldimethylsilyloxy)-4-methoxybenzeneacetonitrile (e.e.>99% (HPLC)) as the cyanohydrin. Yield: 94% (slightly yellow oil).

Analytical data $^1$H-NMR (200 MHz, CDCl$_3$, TMS): −0.15 and 0.03 (s, 6H, Si(CH$_3$)$_2$); 0.88 (s, 9H, C(CH$_3$)$_3$)); 1.9 (broad, 1H, NH); 2.44 (s, 3H, NCH$_3$); 2.59 (dd, ABX, 1H, CH$_2$, J$_{AB}$=11.8 Hz, J$_{AX}$=8.2 Hz); 2.74 (dd, ABX, 1H, CH$_2$, J$_{AB}$=11.8 Hz, J$_{BX}$=4.6 Hz); 3.80 (s, 3H, OCH$_3$); 4.76 (dd, 1H, CH(OTBS), J=4.6 and 8.2 Hz); 6.85 (d, 2H, arom., J=8.7 Hz); 7.23 (d, 2H, arom., J=8.7 Hz). $^{13}$C-NMR (50 MHz, CDCl$_3$, CDCl$_3$): −5.1 and −4.7 (Si(CH$_3$)$_2$); 17.9 (C(CH$_3$)$_2$); 25.6 (C(CH$_3$)$_3$); 35.9 (NCH$_3$); 54.9 (OCH$_3$); 60.6 (CH$_2$); 73.5 (CH(OTBS)); 113.3 (C$_3$ and C$_5$ arom.); 127.0 (C$_2$ and C$_6$ arom.); 135.4 (C$_1$ arom.); 158.6 (C$_4$ arom.) [α]$_D^{20}$ −67°(c=1 CHCl$_3$).

EXAMPLE 9

(R)-(−)-α-[[(1-Methylethyl)aminolmethyl]-4-methoxybenzenemethanol

Prepared in the same manner as in EXAMPLE 7, using iso-propylamine in the transimination reaction.

Yield: 78% of (5 g) (slightly yellow solid). Analytical data $^1$H-NMR (200 MHz, CDCl$_3$, TMS): 1.07 (d, 6H, 2×CH$_3$, J=6.2 HZ); 2.0 (broad, 2H, OH+NH); 2.64 (dd, ABX, 1H, CH$_2$, J$_{AB}$=11.8 Hz J$_{AX}$=9.2 Hz ); 2.83 (sept., 1H, CH(CH$_3$)$_2$, J=6.2 Hz); 2.90 (dd, ABX, 1H, CH$_2$, J$_{AB}$=11.8 Hz J$_{BX}$=3.6 Hz); 3.81 (s, 3H, OCH$_3$); 4.61 (dd, 1H, CH(OH), J=3.6 and 9.2 Hz); 6.88 (d, 2H, arom., J=8.7 Hz); 7.34 (d, 2H, arom., J=8.7 Hz). $^{13}$C-NMR (50 MHz, CDCl$_3$, CDCl$_3$): 22.7 and 22.9 (CH(CH$_3$)$_2$); 48.6 (CH(CH$_3$)$_2$); 54.8 (CH$_2$); 55.1 (OCH$_3$); 71.5 (CH(OH)); 113.6 (C$_3$ and C$_5$ arom.); 126.9 (C$_2$ and C$_6$ arom.); 135.3 (C$_1$ arom.); 158.8 (C$_4$ arom.).

This product was converted into the HCl salt and crystallized from iso-propanol for optical rotation and melting point measurements. [α]$_D^{20}$ −63°(c=1 H$_2$O). mp: 157°-159° C.

EXAMPLE 10

(R)-(−)-α-[[(1-Methylethyl)amino]methyl]-α-[(tert-butyldimethylsilyl)oxy]-4-methoxybenzenemethane Prepared in the same manner as in EXAMPLE 8, using iso-propylamine in the transimination reaction.

Yield: 80% (slightly yellow oil). Analitical data $^1$H-NMR (200 MHz, CDCl$_3$, TMS): −0.17 and 0.04 (s, 6H, Si(CH$_3$)$_2$); 0.88 (s, 9H, C(CH$_3$)$_3$; 1.02 and 1.06 (d, 3H, CH(CH$_3$)$_2$, J=6.2 Hz); 2.2 (broad, 1H, NH); 2.71 (d, 2H, CH$_2$, J=6.3 Hz ); 2.81 (sept., 1H, CH(CH$_3$)$_2$, J=6.2 Hz); 3.80 (s, 3H, OCH$_3$); 4.75 (t, 1H, CH(OTBS), J=6.3 Hz); 6.85 (d, 2H, arom., J=8.2 Hz); 7.23 (d, 2H, arom., J=8.2 Hz) . $^{13}$C-NMR (50 MHz, CDCl$_3$, CDCl$_3$): −5.0 and −4.5 (Si(CH$_3$)$_2$); 17.9 (C(CH$_3$)$_3$); 22.6 and 22.9 (CH(CH$_3$)$_2$); 25.7 (C(CH$_3$)$_3$); 48.2 (CH(CH$_3$)$_2$); 55.0 (OCH$_3$); 56.5 (CH$_2$); 73.9 (CH(OTBS)); 113.4 (C$_3$ and C$_5$ arom.): 127.1 (C$_2$ and C$_6$ arom.): 135.6 (C$_1$ arom. ); 158.7 (C$_4$ arom.). [α]$_D^{20}$ −62°(c=1 CHCl$_3$); e.e.>99% (HPLC)).

EXAMPLE 11

(2R,3E)-(+)-[2(2′-Phenoxy-isopropyl)oxy]pentenenitrile (2R,3E)-(−)-Hydroxypentenenitrile (0.30 g; 3 mmol) was dissolved in toluene (5 ml), and 2-phenoxypropene (0.50 g; 3.75 mmol) was added. A catalytic amount of POCl$_3$ (13 mg) was added and the mixture was stirred overnight at room temperature. After addition of triethylamine (29 mg), the mixture was taken up in diethylether (25 ml) and successively washed with water (5 ml) and a saturated NaHCO$_3$ solution (5 ml). The organic phase was dried (MgSO$_4$), concentrated in vacuo, and chromatographed over silica gel (75 g; eluent-=petr. ether (40°-60° C.):CH$_2$Cl$_2$:EtOAc-:Et$_3$N=14:1:1:1; Rf=0.57), to leave a colorless oil. Yield: 0.67 g (=94%). [α]$_D^{20}$ +68°(c=1 , CHCl$_3$). E.e. 99% (HPLC) . $^1$H-NMR: δ1.48 and 1.69 (s, 6H, CH$_3$); 1.78 (m, 3H, CH$_3$CH); 5.20 (dd, 1H, CH(CN), J=1.0 and 6.4 Hz); 5.61 (m, 1H, CH$_3$CH:CH); 6.05 (m, 1H, CH₃CH:CH); 7.2 (m, 5H, arom). ¹³C-NMR: δ17.4 (CH₃CH); 25.3 and 26.3 (C(CH₃)₂); 60.5 (CH(CN)); 104.3 (C(CH₃)₂); 118.4 (CN); 121.1–132.6 (CH:CH and arom); 154.1 (C₁ arom).

EXAMPLE 12

(2R,3E)-(−)-1-Methylamino-2-(2'-phenoxy-isopropyl)oxypentene

Synthesis of the title compound was accomplished by using the product of EXAMPLE 11 as the starting material in the procedure as described in EXAMPLE 3, carrying out an alkaline work-up.

Yield: 96%. $[\alpha]_D^{20}$ −2.6°(c=1, CHCl₃). E.e. 99% (HPLC). ¹H-NMR: δ1.50 and 1.55 (s, 6H, CH₃); 1.65 (d, 3H, CH₃CH); 2.39 (s, 3H, NCH₃); 2.60 and 2.74 (ABX, 2H, CH₂, $J_{AB}$=−11.8, $J_{AX}$=5.7 and $J_{BX}$=6.2 Hz); 4.50 (m, 1H, CH(OR)); 5.60 (m, 2H, CH:CH); 7.2 (m, 5H, arom). ¹³C-NMR: δ17.6 (CH₃); 26.5 and 26.8 (C(CH₃)₂); 36.2 (NCH₃); 56.6 (CH₂); 72.6 (CH(OR)); 103.9 (C(CH₃)₂); 120.9–131.9 (CH:CH and arom); 155.3 (C₁ arom).

EXAMPLE 13

(2R,3E)-(−)-2-Hydroxy-1-methylaminopentene

To a solution of the product of EXAMPLE 12 (220 mg; 0.88 mmol) in diethylether (25 ml) was added a 0.1N HCl solution (20 ml; 2 mmol). After shaking for 30 sec, the two layers were separated. The water layer was made alkaline (pH>10), and extracted with CH₂Cl₂ (3×25 ml). The organic phase was washed with water (5 ml; pH>10), dried (K₂CO₃), and concentrated in vacuo. Yield: 63.1 mg (=62%). $[\alpha]_D^{20}$−24°(c=1, CHCl₃). ¹H-NMR: δ1.70 (d, 3H, CH₃CH); 2.43 (s, 3H, NCH₃); 2.60 (m, 2H, CH₂); 3.00 (broad, 2H, NH and OH); 4.12 (m, 1H, CH(OH)); 5.45 (m, 1H, CHCH(OH)); 5.74 (m, 1H, CH₃CH). ¹³C-NMR: δ17.6 (CH₃); 35.8 (NCH₃); 57.2 (CH₂); 70.0 (CH(OH)); 127.2 and 131.9 (CH:CH).

EXAMPLE 14

Bis-[(R)-1-(tert.-butyldimethylsilyl)oxy-1-phenylethan-2-yl]-amine; compound 11

Formula:
compound 11: R=H
compound 12: R=CH₃

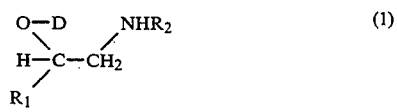

To a solution of 9.90 g (40 mmol) (R)-TBS-mandelonitrile (TBS=tert.-butyldimethylsilyl) in 300 ml dry diethylether was added 80 ml of a solution of 1M DIBAL (80 mmol) in hexane at −80° C. The reaction mixture was stirred at −60° C. to −80° C. for 3 hours. Then successively 50 ml dry methanol and a solution of 25.1 g (100 mmol) (R)-1-[(tert.-butyldimethylsilyl)oxy-1-phenylethan-2-yl]amine in 25 ml methanol were added at −90° C. After stirring at room temperature for 2 hours, the reaction mixture was brought to 0° C. NaBH₄ (3.00 g; 80 mmol) was added in small portions, after which the mixture was stirred overnight at ambient temperature. Water (500 ml) was added and the layers were separated. The water layer was extracted twice with diethylether (300 ml). The organic layers were washed with a saturated NaCl solution, dried on MgSO₄ and evaporated. Purification by flash column chromatography (eluent: triethylamine/petr. ether 40–60=3/97) yielded 17.8 g (92%) of the title compound. $[\alpha]_D^{20}$−72°(c=1, CHCl₃). E.e.: 90% (HPLC). ¹H-NMR: δ7.27 (m, 10H, arom); 4.77 (dd, 2H, J=5.4 Hz, J=7.9 Hz, CH); 2.88 (dd, 2H, J=7.7 Hz, J=11.9 Hz, CH₂), 2.65 (dd, 2H, J=5.4 Hz, J=11.9 Hz, CH₂); 1.62 (bs, 1H, NH); 0.83 (s, 18H, t-Bu); −0.01 (s, 6H, SiCH₃); −0.17 (s, 6H, SiCH₃). ¹³C-NMR: δ143.6, 128.1, 127.3, 126.1 (arom), 74.5 (CH), 58.7 (CH₂), 25.9 (C(CH₃)₃), 18.1 (C(CH₃)₃), −4.6, −4.8 (SiCH₃).

EXAMPLE 15

[(R)-1-(tert.-Butyldimethylsilyl)oxy-1-phenylethan-2-yl][1R,2S)-1-(tert.-butyldimethylsilyl)oxy-1-phenylpropan-2-yl)amine: compound 12; see above formula The title compound was prepared in a corresponding manner as described in EXAMPLE 14, using TBS-(1R, 2S)-norephedrine in the transimination reaction.

Yield: 89%. $[\alpha]_D^{20}$−59°(c=1, CHCl₃). ¹H-NMR: δ7.25 (m, 10H, arom); 4.71 (dd, J=4.8 Hz, J=7.5 Hz, OCHCH₂); 4.49 (d, 1H, J=5.7 Hz, OCHCH); 2.74 (m, 3H, CHN+CH₂N); 1.51 (bs, 1H, NH); 1.03 (d, 3H, J=6.2 Hz, CH₃); 0.85 (s, 9H, t-Bu); 0.77 (s, 9H, t-Bu), 0.02 (s, 3H, SiCH₃); −0.10 (s, 3H, SiCH₃); −0.23 (s, 3H, SiCH₃); −0.25 (s, 3H, SiCH₃). ¹³C-NMR: δ143.9, 142.8, 128.0, 127.2, 127.1, 126.1 (arom), 78.1, 75.3 (CHO), 60.0 (CHN), 56.8 (CH₂N), 25.8 (C(CH₃)³), 18.0 (C(CH₃)₃), 18.1 (C(CH) 3)₃), 15.6 (CH₃), −4.1, −4.6, −4.9 (SiCH₃).

We claim:

1. Method for the preparation of an N-substituted vicinal aminoalcohol derivative of formula 1

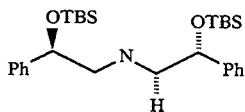

(1)

wherein

D is a group protecting the hydroxy group;

R₁ is optionally selected from the group consisting of phenyl, naphthyl, benzofuryl, benzodioxanyl and benzodioxolyl which is substituted with one or more groups X, wherein X is hydroxy, alkoxy(1–5C), alkyl(1–5C)carbonyloxy, amino, alkyl(1–5C)carbonylamino, alkyl(1–5C)sulphonylamino, nitro, alkyl(1–5C)sulphonyl, alkyl(1–5C)carbonyl, halogen, cyano, alkyl(1–5C) or cycloalkyl(5–12C), or wherein R₁ is a saturated or unsaturated straight or branched alkyl group having 1–30 C-atoms which may be substituted with halogen, alkoxy(1–5C), alkylthio(1–5C), phenyl or phenoxy optionally substituted with one or more groups X, and R₂ is a hydrogen atom or a saturated or unsaturated straight or branched alkyl(1–10C) group, optionally substituted with halogen, hydroxy, alkoxy(1–4C) or OD, or a phenyl, phenylalkyl(7–10C) or heteroarylalkyl(1–3C for the alkyl) group, wherein the heteroaryl is selected from the group consisting of benzofuryl, benzodioxanyl and benzodioxolyl, optionally substituted with one to three groups X, or wherein R₂ has the formula 7

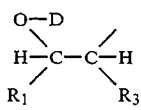 (7)

wherein $R_3$ is hydrogen or alkyl(1-4C);

is prepared by reacting a hydroxy-protecting cyanohydrin derivative of formula 2

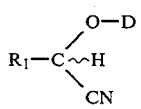 (2)

with a reducing reagent of formula 3

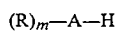 (3)

wherein

A represents a hydrogen atom or a metal atom selected from the group consisting of alkali, earth alkali or early transition metal atoms, R is an alkyl(1-6C), alkoxyalkyl(1-6C) or alkoxyl(1-6C) group, and m is, dependent on the valence of A, 0-2; yielding a partially reduced compound of formula (4)

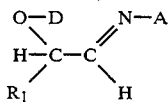 (4)

followed by a transimination reaction using a primary amine of formula 5

 (5)

and reduction of the resulting imine, wherein D, $R_1$ and $R_2$ have the abovementioned meanings;

with the proviso that, if $R_2$ is a hydrogen atom, the transimination reaction step is omitted.

2. Method according to claim 1 wherein use is made of one of the enantiomers of the compound of formula 2 thereby yielding an optically pure derivative of the compound according to formula 1.

3. Method for the preparation of a compound of formula 8

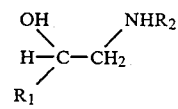 (8)

by using the method according to claim 1 and subsequently removing the hydroxyl-protecting group D of the compound of formula 1, wherein D, $R_1$, and $R_2$ have the meanings given in claim 1.

4. Method according to claim 3 wherein D is removed without intermediate isolation of the formula 1 compound during a work-up step following the reduction of the imine.

5. Method for the preparation of a compound of formula 8

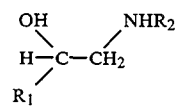 (8)

by using the method according to claim 2 and subsequently removing the hydroxyl-protecting group D of the compound of formula 1.

6. Method according to claim 5 wherein D is removed without intermediate isolation of the formula 1 compound during a work-up step following the reduction of the imine.

* * * * *